(12) United States Patent
Feith et al.

(10) Patent No.: US 12,350,464 B2
(45) Date of Patent: *Jul. 8, 2025

(54) NEEDLELESS CONNECTOR HAVING CHECK VALVE WITH LIP SEAL

(71) Applicant: CareFusion 303, Inc., San Diego, CA (US)

(72) Inventors: Raymond Feith, Chino Hills, CA (US); Chris J. Zollinger, Chino Hills, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/626,966

(22) Filed: Apr. 4, 2024

(65) Prior Publication Data

US 2024/0245901 A1 Jul. 25, 2024

Related U.S. Application Data

(63) Continuation of application No. 16/943,885, filed on Jul. 30, 2020, now Pat. No. 11,986,619.

(51) Int. Cl.
*A61M 39/24* (2006.01)
*A61M 39/26* (2006.01)

(52) U.S. Cl.
CPC ....... *A61M 39/24* (2013.01); *A61M 2039/267* (2013.01); *A61M 2205/0216* (2013.01)

(58) Field of Classification Search
CPC ............... A61M 39/24; A61M 39/26; A61M 2039/267; A61M 2039/268; A61J 1/201; A61J 1/1406; A61J 1/2006; A61J 1/2062
See application file for complete search history.

(56) References Cited

U.S. PATENT DOCUMENTS

| | | | |
|---|---|---|---|
| 4,710,168 A | 12/1987 | Schwab et al. | |
| 5,549,651 A | 8/1996 | Lynn | |
| 8,840,577 B1 | 9/2014 | Zollinger | |
| 11,986,619 B2 * | 5/2024 | Feith | A61M 39/24 |
| 2010/0249725 A1 | 9/2010 | Cote, Sr. | |

(Continued)

FOREIGN PATENT DOCUMENTS

| | | |
|---|---|---|
| EP | 2777759 A1 | 9/2014 |
| JP | 2000-217929 A | 8/2000 |

(Continued)

OTHER PUBLICATIONS

Japanese Office Action for Application No. 2023-505363, dated Mar. 28, 2025, 7 pages including translation.

*Primary Examiner* — Catharine L Anderson
*Assistant Examiner* — Jihad Dakkak
(74) *Attorney, Agent, or Firm* — Morgan, Lewis & Bockius LLP

(57) ABSTRACT

A valve member for a connector includes a head portion, a body portion, and a circumferential lip seal extending radially outward from an outer surface of the head portion. The head portion includes a top section defining a first seal portion. The body portion extends longitudinally from the head portion and defines a second seal portion at a proximal end thereof. The second seal portion is disposed distally to the first seal portion. The circumferential lip seal is disposed between the first and second seal portions.

20 Claims, 3 Drawing Sheets

(56) References Cited

U.S. PATENT DOCUMENTS

| | | | | |
|---|---|---|---|---|
| 2014/0276215 A1* | 9/2014 | Nelson | ................ | A61M 39/223 |
| | | | | 600/573 |
| 2014/0276466 A1* | 9/2014 | Yeh | ...................... | A61M 39/26 |
| | | | | 604/256 |
| 2017/0290216 A1 | 10/2017 | Truitt et al. | | |

FOREIGN PATENT DOCUMENTS

| | | | |
|---|---|---|---|
| JP | 2001-506156 A | 5/2001 |
| JP | 2016-510652 A | 4/2016 |
| JP | 2016-515007 A | 5/2016 |

\* cited by examiner

NEEDLELESS CONNECTOR HAVING CHECK VALVE WITH LIP SEAL

CROSS REFERENCE TO RELATED APPLICATION

This application is a continuation of U.S. patent application Ser. No. 16/943,885, entitled "Needleless Connector Having Check Valve with Lip Seal," filed Jul. 30, 2020, the disclosure of which is incorporated herein by reference in its entirety.

TECHNICAL FIELD

The present disclosure relates generally to needleless connectors, and, in particular, to needleless connectors with a valve member having a sealing lip.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

Due to the nature of currently existing and/or prior art needleless valve geometries, fluid is commonly deposited on the face of the valve head upon removal of a medical implement (e.g., a mating male luer) used to apply an axial force to place the valve member in an open position. In these currently existing needleless valves, fluid deposited on the valve head will occasionally separate from the valve member and flow into the fluid path for administering to a patient, thereby causing anxiety along with potential blood stream diseases.

The description provided in the background section should not be assumed to be prior art merely because it is mentioned in or associated with the background section. The background section may include information that describes one or more aspects of the subject technology.

SUMMARY

In accordance with some embodiments of the present disclosure, a valve member for a connector may include a head portion including a top section defining a first seal portion, and a body portion extending longitudinally from the head portion and defining second seal portion at a proximal end thereof. The second seal portion may be disposed distally to the first seal portion. The valve member may further include a circumferential lip seal extending radially outward from an outer surface of the head portion. The circumferential lip seal may be disposed between the first and second seal portions.

In accordance with some embodiments of the present disclosure, a needleless connector may include a housing having a proximal end defining an inlet port of the housing, a distal end including a base defining an outlet port of the housing, and an inner surface defining an internal cavity extending between the inlet and outlet ports. The needleless connector may further include a resilient valve disposed within at least a portion of the internal cavity and movably retained within the housing. The resilient valve may include a head portion including a top section and a body portion extending distally from the head portion; and a circumferential lip seal extending radially outward from an outer surface of the head portion and disposed between the top section and the body portion. In an open state of the resilient valve where a gap exists between the inner surface of the housing and the outer surface of the head portion, the circumferential lip seal may engage at least a portion of the inner surface of the housing to obstruct fluid from flowing from the internal cavity towards and onto the top section of the head portion.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
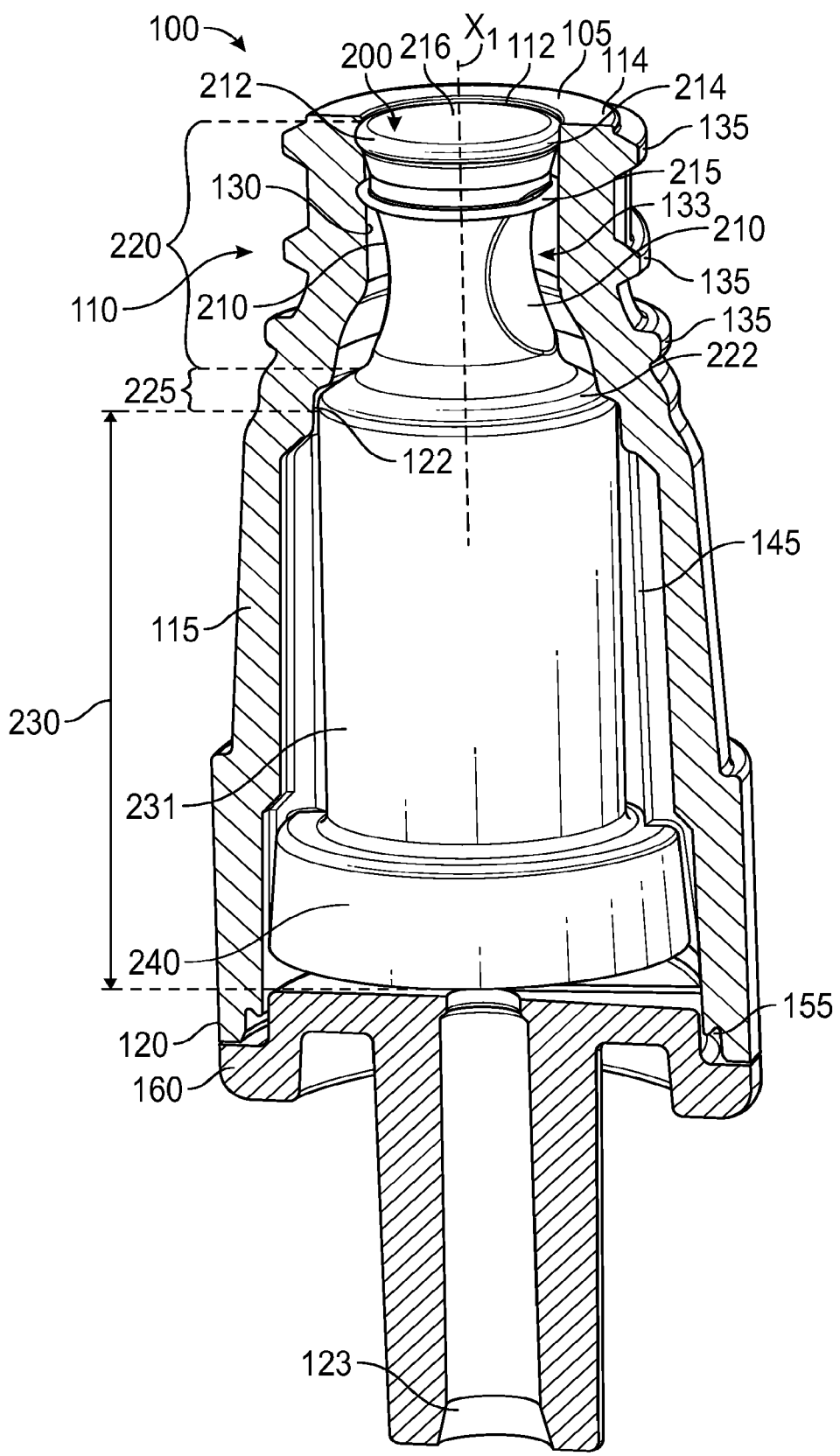
FIG. 1 is a perspective view of a partial cutaway of a housing of a needleless connector having a resilient valve installed therein, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are generally directed to a self-sealing, needleless connector that incorporates a resilient, compressible valve disposed within a housing of the connector, in which the resilient valve has a circumferential lip seal that acts as a wiper or dam that engages the inner surface (inner diameter) of the housing to prevent fluid from moving from the cavity toward the top of the valve via a temporary gap created between the valve and the housing when the valve is canted, tilted, depressed, or otherwise compressed.

More particularly, various embodiments of the present disclosure are directed to a needleless connector having a housing and a compressible valve configured such that when subject to an axial force, tilting of the head portion of the compressible valve (which forms the fluid flow path in existing needleless connectors) is eliminated.

According to various embodiments of the present disclosure, when the axial force is removed, the resilient valve begins to expand to return to its position within the housing in the sealed configuration. As the resilient valve expands, the circumferential lip seal engages the inner surface of the housing and inverts or otherwise bends thereby acting as a wiper or dam that prevents fluid from moving from the cavity of the housing toward the valve face via the temporary gap. Accordingly, the configuration of the valve member of the various embodiments described herein having the circumferential lip seal is advantageous as it prevents droplets of fluid from collecting on the top surface of the valve by obstructing fluid from moving from the cavity to the top surface via the temporary gap. As the circumferential lip seal minimizes the fluid capable of being deposited on the valve face, it advantageously prevents anxiety along with potential blood stream diseases commonly associated with fluids deposited on the valve face (top surface) of the valve head.

While the following description is directed to the administration of medical fluid to a patient by a medical practitioner using the disclosed needleless connector, it is to be understood that this description is only an example of usage and does not limit the scope of the claims.

FIG. 1 is a perspective view of a partial cutaway of a housing 110 of a needleless connector 100 having a resilient valve installed therein, in accordance with some embodiments of the present disclosure. As depicted, the housing 110 may have a proximal end 105 defining an inlet port 112 of the housing 110 and a distal end 120 including a base portion 160 defining an outlet port 123 of the housing 110, In some embodiments, the housing 110 may further include an inner surface 130 defining an internal cavity 133 which extends at least partially between the proximal and distal ends 105 and 120 of the housing 110. The housing 110 may be formed of a body portion 115 coupled to or otherwise integrally formed with the base portion 160. However, in some embodiments, the housing 110 may be formed from a combination of other pieces or parts similarly dimensioned to house the resilient valve 200 therein. In operation, a fluid pathway may be established through needleless connector 100 from the inlet port 112 to the outlet port 123, for example. As referred to herein, proximally refers to an orientation toward the inlet port 112 of the housing 110, and distally refers to an orientation toward the base portion 160 or bottom of the housing 100, opposite the inlet port 112.

As depicted, in addition to housing 110 including the inlet port 112 of the housing 110 for interfacing with a medical implement (e.g., a male luer 300 (illustrated in FIG. 4)), the housing 110 may further include an opening 155 for connecting with the base 160 of the housing 110. As depicted, body portion 115 of the housing 110 may include one or more fluid flow channels 144 and one or more interior support columns (not shown). The lower section of the body portion 115 (e.g., a section proximal to the opening 155) may have an increased diameter and include one or more internal contact tabs (not shown). When assembled in a needleless connector 100, the one or more internal contact tabs may provide a radial force substantially orthogonal to a central longitudinal axis X1 of the housing 110 onto a flange portion of the resilient valve 200 that is arranged on a valve mount of the base portion 160.

In accordance with various embodiments of the present disclosure, the inlet port 112 may include a top port surface 114 and a channel defined in the internal cavity 133. The inlet port 112 may include engagement features 135 for coupling to another device (e.g., a fluid transfer assembly). For example, engagement features 135 may include cooperating mechanical elements, such as internal or external surface threads, detents, bayonet-type locking elements, etc., as well as other surface configurations, such as a tapered Luer surface for frictional engagement. In some embodiments, the inlet port 112 may define a female luer fitting with luer lock threading 135. The inner surface 130 and the internal cavity 133 defined therein may extend longitudinally from the opening of the top port surface 114 of the inlet port 112 into the body portion 115 of the housing 110.

In some embodiments, an internal sealing edge 122 may be defined on the inner surface 130 of the housing 110. The internal sealing edge 122 may be a circumferential edge and configured for retaining the resilient valve 200 within the internal cavity 133 of the assembled needleless connector 100. In operation, the internal sealing edge 122 may be arranged to provide blocking of fluid flow in conjunction with a primary seal portion 225 of the compressible valve 200.

Figure 2:
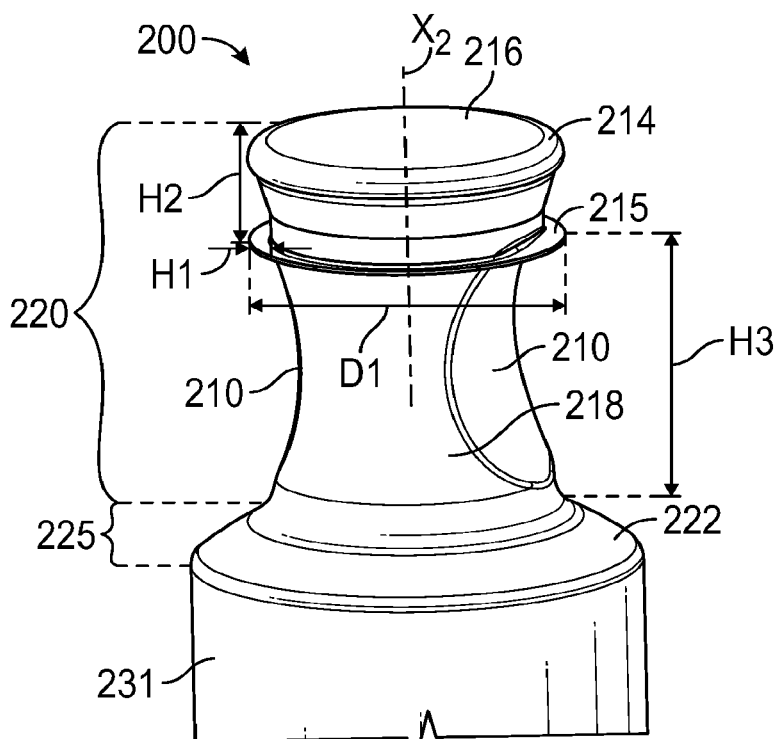
FIG. 2 is a perspective view illustrating an example of a resilient valve of a needleless connector, in accordance with some embodiments of the present disclosure.

FIG. 2 is a perspective view illustrating an example of a resilient valve of a needleless connector, in accordance with some embodiments of the present disclosure. FIG. 2 illustrates in isolation an example resilient valve 200. Resilient valve 200 may include head portion 220, and body portion 230 extending distally from the head portion 220. In certain embodiments, the head portion 220 includes a column section 218 which may define an axial center $X_2$ of the resilient valve 200. The axial center $X_2$ may substantially correspond to the central longitudinal axis X1 of the needleless connector housing 100 when assembled therein in a closed state of the resilient valve 200. In a non-activated state (e.g., in isolation or within a connector but not displaced by a medical implement) the axial center $X_2$ may extend longitudinally through the head portion 220 and the body portion 230 of the compressible valve 200 (as depicted in FIG. 1). In the aforementioned state, the body portion 230 of the compressible valve 200 may have the same axial center as the head portion 220 or other portions of the compressible valve 200. However, as described in further detail below, in an activated state (e.g., when an axial force is applied to the compressible valve 200 using the medical implement, for example male luer 300) the axial center $X_2$ of the resilient valve 200 may change and pivot in relation to the central longitudinal axis X1 upon the resilient valve 200 being activated by the medical implement.

In accordance with some embodiments, the head portion 220 may include a top section 212 defining a first or secondary seal portion 214 of the resilient valve 200. The body portion 230 may further define a second or primary seal portion 225 at a proximal end of the body portion 230. As depicted, the primary seal portion 225 may be disposed distally to the secondary seal portion 214.

According to various aspects of the present disclosure, the head portion 220 may further include a circumferential lip seal 215 extending radially outward from an outer surface of the head portion 220. As depicted, the circumferential lip seal 215 may protrude radially outward from the outer surface of the head portion 220 towards the inner surface 130 of the housing 110. The circumferential lip seal 215 may be a thin, flexible member which engages the inner surface 130 of the housing 110 of connector 100. For example, as shall be discussed in further detail below, the circumferential lip seal 215 may form a thin seal (in the order of 0.0005-0.005 inches) that will prevent fluid from flowing from the internal cavity 133 to the valve face (i.e., top surface 216) during removal of the medical implement (e.g., syringe 300). Accordingly, the circumferential lip seal 215 may function to obstruct most of the fluid flowing from the internal cavity from reaching the top surface 216 of the valve 200 during removal of the medical implement 300. The aforementioned thin and flexible configuration of the circumferential lip seal 215 is advantageous as the circumferential lip seal 215 is thin enough to be inverted during syringe insertion and to slide with minimal drag force during syringe removal. Accordingly, the circumferential lip seal 215 may allow fluid to move in one direction. For example, the circumferential lip seal 215 my allow fluid to flow or otherwise drain from a first cavity 145 formed between the circumferential lip seal 215 and the secondary seal portion 214 toward a second cavity 165 formed between the circumferential lip seal 215 and the primary seal portion 225.

In some embodiments, a distance H1 that the circumferential lip seal 215 extends radially outward from the outer surface of the head portion 220 may be smaller or shorter than a distance H2 between the circumferential lip seal 215 and the first (secondary) seal portion 214. The aforementioned configuration allows for the circumferential lip seal 215 to bend or otherwise deflect upwards towards the secondary seal portion without the risk of breaching or otherwise becoming lodged between the inner surface of the housing 130 as the valve 200 expands from the open to the closed state.

In some embodiments, the circumferential lip seal 215 may be disposed between the first (secondary) and second (primary) seal portions 214 and 225. In particular, as depicted the circumferential lip seal 215 may be disposed at a position closer to the secondary seal portion 214 than the primary seal portion 225. For example, a distance or height H2 may be defined between the circumferential lip seal 215 and the secondary seal portion 214. Similarly, a distance or height H3 may be defined between the circumferential lip seal 215 and the secondary seal portion 214. In some embodiments, the distance or height H2 may be shorter or smaller than the distance or height H3. The aforementioned configuration is advantageous in order to minimize the volume of fluid which may collect in the first cavity 145.

The top section 212 may include a top planar surface 216 which is oriented perpendicularly with respect to the axial center $X_2$ of the column section 218. In some embodiments, as depicted in FIG. 2, the circumferential lip seal 215 may be oriented parallel to and/or concentrically disposed with respect to the top planar surface 216. The various embodiments of the present disclosure however, are not limited to the aforementioned configuration. In other embodiments, the circumferential lip seal 215 may be oriented at a non-parallel angle with respect to the top planar surface 216. In these embodiments, during syringe insertion when the head portion 220 is subject to the axial force F (illustrated in FIG. 4) causing the head portion 220 to cant, bend or otherwise deflect as illustrated, the circumferential lip seal 215 may be oriented such that it is parallel to the top port surface 114. This configuration may be advantageous as the maximum or entire perimeter of the circumferential lip seal 215 may contact the inner surface 130 of the housing at same time. Accordingly, sealing capabilities of the circumferential lip seal 215 may be optimized as the entire perimeter of the circumferential lip seal 215 engages the inner surface 130 of the housing 110.

As previously described above, and as illustrated in FIGS. 1 and 2, the column section 218 may define the axial center $X_2$ of the head portion 220, and the circumferential lip seal 215 may be oriented substantially perpendicularly with respect to the axial center X of the head portion. The aforementioned configuration allows maximum exposure and engagement of the circumferential lip seal 215 with the inner surface 130 of the housing when the resilient valve is in the closed position. In other embodiments, however, the circumferential lip seal 215 may be oriented at a non-perpendicular angle with respect to the axial center of the head portion. For example, in some embodiments, the circumferential lip seal 215 may be oriented at an angle such that when the head portion 220 is subject to the axial force F causing the head portion 220 to cant, bend or otherwise deflect, the circumferential lip seal 215 may be oriented such that the maximum or entire perimeter of the circumferential lip seal 215 may contact the inner surface 130 of the housing at same time. Accordingly, sealing capabilities of the circumferential lip seal 215 may be optimized as the entire perimeter of the circumferential lip seal 215 engages the inner surface 130 of the housing 110.

According to various embodiments of the present disclosure, the head portion 220 may include at least one notch 210 disposed along the outer surface of the column section 218. As depicted in FIG. 2, the column section 218 may have a generally solid cylindrical section. As can be seen with respect to the longitudinal cross-sectional view of FIG. 3, the at least one notch 210 may be in the form of an arcuate-shaped recess within the column section 218. However, it is to be appreciated that the implementations of the notch(es) 210 may comprise a variety of shapes and sizes, such as, but not limited to, notches having triangular or various geometric cross-sections.

In some embodiments, the head portion 220 of the resilient valve 200 may not include a notch, but rather may have a discontinuity segment disposed on the column section 218. For example, a side or a portion of a side of the column section may be formed of a different material (or a same material with a different hardness value) than the remainder of the column section. Additionally, a side or a portion of a side of the column section may be hollow, while the other side or portion of the remainder of the column section may be solid. Thus, an effective change in the resiliency with respect to the movement of the head (similar to that of a removed or extracted volume of a notch) may result. It is to be understood that while the notches 210 are shown generally opposite each other on the column section 218, other arrangements of the at least one notch 210 on the column section 218, including three or more notches, are contemplated.

According to various embodiments of the present disclosure, the resilient valve 200 may include any of the various materials used for producing mechanical valves for needleless connectors and other medical implements. In some implementations, the head portion 220 may include an elastomeric material, such as but not limited to, a silicone compound. Moreover, the primary seal portion 225 and lower portion 230 may include an elastomeric material. In some embodiments, all or some of the flexible valve may be formed of liquid silicone rubbers.

Additionally, according to various embodiments, the elastomeric material of the head portion 220 may have a higher durometer value than the elastomeric material of the lower portion 230. For example, the collapsing functionality of the lower portion 230 associated with facilitating a fluid flow path in the needleless connector 100 may benefit from a more pliable material or composition attributes for operation, whereas the head portion 220 and primary seal portion 230 may require a more rigid construction for disengaging the primary seal 225.

In accordance with some embodiments, and referring again to FIGS. 1 and 2, the primary seal portion 225 may have a cross-sectional area greater than a cross-sectional area of the column section 218 of the head portion 220. For example, the primary seal portion 225 may be in the form of a frustoconical surface 222 for engaging with the internal sealing edge 122 of the connector housing 110. The frustoconical shape of the primary seal portion 225 may be configured such that a first cross-sectional area of the primary seal portion 225 proximal the head portion 220 is smaller than a second cross-sectional area of the primary seal portion 225 distal to the head portion 210. In other words, the primary seal portion 225 may be narrower towards the head portion 220 and wider towards the lower portion 230.

In some embodiments, the lower portion 230 may be in the form of an elongated tubular member 231 having a closed end proximal the primary seal portion 225 and an open end distal the primary seal portion 225. As such, an interior air space may be defined in the interior of the resilient valve 200. According to some aspects, the resilient valve 200 may be collapsible in operation with a needleless connector assembly. In these embodiments, the lower portion 230 may include various dimples and/or incisions to facilitate proper collapsing functionality in accordance with different embodiments of the present disclosure. Moreover, while the head portion 220 of the resilient valve 200 may have generally cylindrical properties allowing it to operate with a male luer-tapered tip of a medical implement or similar interconnection device, the lower portion 230 may be in the form of a plurality of shapes, sizes, and characteristics associated with the functionality and operation of the resilient valve in conjunction with the needleless connector apparatus in which it is used. In some embodiments, when the lower portion 230 has a tubular section 231, this section 231 may comprise a plurality tubular shapes, such as, but not limited to, cylindrical, rectangular, hexagonal, tubular shapes.

Figure 3:
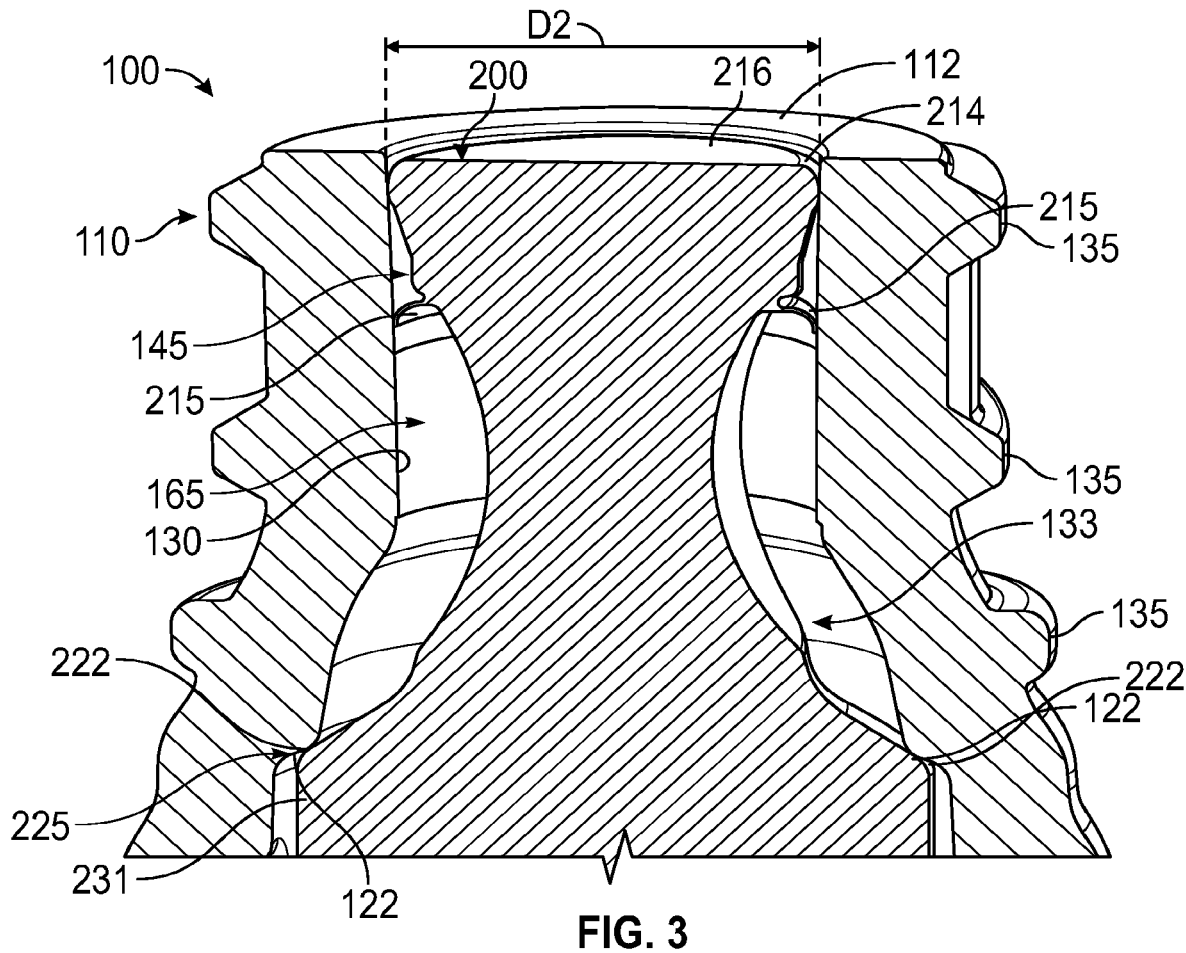
FIG. 3 is a partial cross-sectional view of the assembled needleless connector housing and compressible valve of FIG. 1 in a closed position, in accordance with some embodiments of the present disclosure.

FIG. 3 is a partial cross-sectional view of the assembled needleless connector 100 with housing 110 and compressible valve 200 of FIG. 1 in a closed position before insertion of a medical implement, in accordance with some embodiments of the present disclosure. Referring to FIG. 3 with continued reference to FIG. 1, the assembled needleless connector 100 as illustrated in FIG. 3 is in a sealed configuration such that any fluid from an interconnected fluid path coupled to the outlet port 123 is sealed from the inlet port 112. In some embodiments, the needleless connector 100 may be assembled such that the flange portion 240 of the compressible valve 200 is coupled, snapped, or otherwise attached onto a valve mount of the base portion 160.

The internal cavity 133 of the housing 110 may be arranged on top of the compressible valve 200 coupled to the base portion 160 such that the head portion 220 of the compressible valve 200 is aligned and disposed within the inlet port 112. Upon assembly, the top surface 216 of the head portion 220 of the compressible valve 200 may have a resulting plane that is substantially perpendicular to the central longitudinal axis $X_2$ or axial center of the column section 218 of the head portion 220 when the head portion 220 is engaged within the inlet port 112 of the housing 110. Additionally, the one or more internal contact tabs (not shown) disposed on the lower section of the body portion 115 of the housing 110 may surround and apply pressure to a sidewall of the flange portion 240 to secure and/or anchor the compressible valve 200 in the housing 110. In operation, the resilient valve 200 of the needleless connector can compress, collapse, cant and/or fold when the axial force F (illustrated in FIG. 4) is applied to the top surface 216 of the compressible valve 200 and expand and realign when the axial force is removed, as shall be described in further detail below.

Accordingly, the one or more internal contact tabs (not shown) may provide a radial force substantially orthogonal to the central longitudinal axis $X_2$ onto the sidewall of the flange portion 240. In this regard, when the axial force F is applied to the top surface 216 of the head portion 220 of the compressible valve 200, the effect of any resulting axial force through the compressible valve 200 onto the base portion 120 of the housing 100 is reduced if not eliminated. Such a resulting axial force applied onto the base portion 120 can work against or in derogation, for example, to a fused connection between the base portion 120 and the body portion 115, and over time may disadvantageously cause the fused connection to become breached and/or separated.

Figure 4:
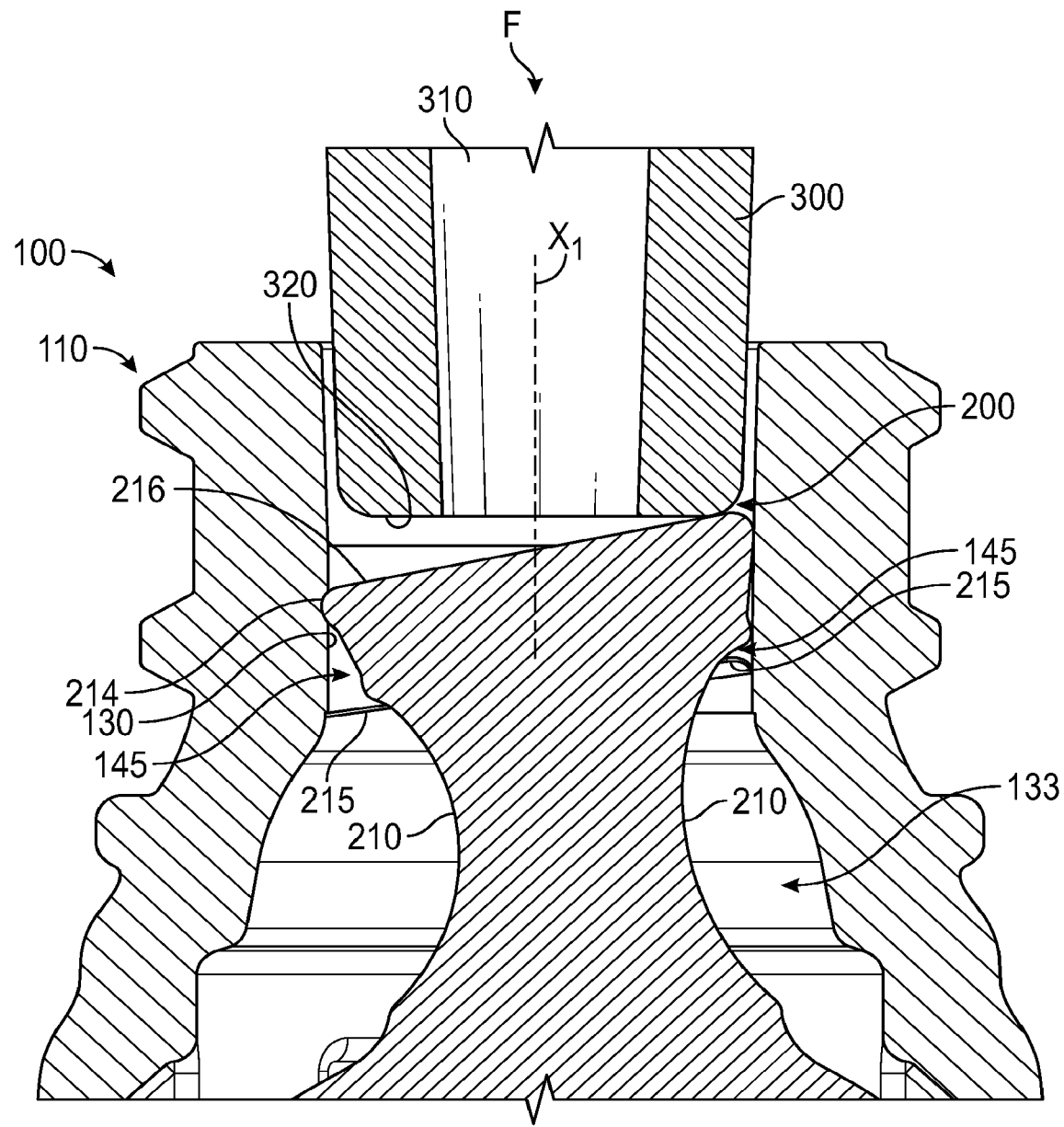
FIG. 4 is a cross-sectional view of a partial cutaway of a housing of a needleless connector having a compressible valve installed therein with an axial force applied to place the valve in an open position, in accordance with some embodiments of the present disclosure.

FIG. 4 is a cross-sectional view of a partial cutaway of a housing of a needleless connector having a compressible valve installed therein with an axial force applied to place the valve in an open position, in accordance with some embodiments of the present disclosure. FIG. 4 provides a longitudinal cross-sectional view of needleless connector 100 showing the resilient valve 200 upon initial entry of a medical implement 300 into the inlet port 112. As the medical implement 300 (e.g., a syringe) is initially inserted into the inlet port 112 of the needleless connector 100, an axial force F is exerted onto the resilient valve 200 such that the resilient valve is displaced distally causing the frustoconical surface 222 of the primary seal portion 225 to separate from the internal sealing edge 122.

As the axial force F continues to be applied, the medical implement 300 may descend further into the inlet port 112, the head portion 220 of valve 200 may further compress, collapse, cant, and/or fold. As one of the notches 210 folds or collapses, the other notch 210 may open or expand such that the top surface 216 may tilt downwardly (distally) as illustrated in FIG. 4). Accordingly, a temporary gap may be formed between the inner surface 130 of the housing 110 and the head portion 220 of the resilient valve 200. In this regard, a fluid path from the medical implement 300 in the inlet port 112 may be established through the interior of the needleless connector 100 to the outlet port 123. For example, a fluid path may be established between the inlet port 112 and the outlet port 123 via the internal cavity 133.

As the medical implement 50 is removed from the first port 252, the resilient valve 100 may begin to expand to return to its position within the housing in the sealed configuration as illustrated in FIG. 3. As the resilient valve expands, the circumferential lip seal 215 engages the inner surface 130 of the housing 110 and inverts or otherwise bends thereby acting as a wiper or dam that prevents fluid from moving from the cavity 133 toward the top surface 216 of the valve 200 via the temporary gap. Accordingly, the configuration of the valve member of the various embodiments described herein having the circumferential lip seal 215 is advantageous as it prevents droplets of fluid from collecting on the top surface 216 of the valve 200 by obstructing fluid from moving from cavity 133 to top surface 216 via the temporary gap.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: A valve member for a connector, the valve member comprising: a head portion including a top section defining a first seal portion; a body portion extending longitudinally from the head portion and defining second seal portion at a proximal end thereof, wherein the second seal portion is disposed distally to the first seal portion; and a circumferential lip seal extending radially outward from an outer surface of the head portion, the circumferential lip seal disposed between the first and second seal portions.

Clause 2: The valve member of Clause 1, wherein the circumferential lip seal comprises a flexible member configured to engage an inner surface of the connector and to deflect as the valve member reciprocates within the connector.

Clause 3: The valve member of Clause 1, wherein a distance between the circumferential lip seal and the first seal portion is smaller than a distance between the circumferential lip seal and the second seal portion.

Clause 4: The valve member of Clause 1, wherein a distance that the circumferential lip seal extends radially outward from the outer surface of the head portion is smaller than a distance between the circumferential lip seal and the first seal portion.

Clause 5: The valve member of Clause 1, wherein the top section includes a top planar surface and the circumferential lip seal is oriented parallel to the top planar surface.

Clause 6: The valve member of Clause 1, wherein the top section includes a top planar surface and the circumferential lip seal is oriented at a non-parallel angle with respect to the top planar surface.

Clause 7: The valve member of Clause 1, wherein the head portion further comprises a column section defining an axial center of the head portion, and the circumferential lip seal is oriented substantially perpendicularly with respect to the axial center of the head portion.

Clause 8: The valve member of Clause 1, wherein the head portion further comprises a column section defining an axial center of the head portion, and the circumferential lip seal is oriented at a non-perpendicular angle with respect to the axial center of the head portion.

Clause 9: The valve member of Clause 1, wherein the head portion further comprises a column section defining an axial center of the head portion, the column section further defining at least one notch disposed along the outer surface of the head portion.

Clause 10: The valve member of Clause 1, wherein at least one of the head portion or the circumferential lip seal comprises an elastomeric material.

Clause 11: The valve member of Clause 1, wherein the circumferential lip seal comprises silicone or a silicone compound.

Clause 12: A needleless connector, comprising: a housing having a proximal end defining an inlet port of the housing, a distal end including a base defining an outlet port of the housing, and an inner surface defining an internal cavity extending between the inlet and outlet ports; and a resilient valve disposed within at least a portion of the internal cavity and movably retained within the housing, the resilient valve comprising: a head portion including a top section and a body portion extending distally from the head portion; and a circumferential lip seal extending radially outward from an outer surface of the head portion and disposed between the top section and the body portion, wherein in an open state of the resilient valve where a gap exists between the inner surface of the housing and the outer surface of the head portion, the circumferential lip seal engages at least a portion of the inner surface of the housing to obstruct fluid from flowing from the internal cavity towards and onto the top section of the head portion.

Clause 13: The needleless connector of Clause 12, wherein the body portion of defines a primary seal portion at a proximal end thereof, the top section of the head portion defines a secondary seal portion, and the circumferential lip seal comprises a seal positioned between the primary and secondary seal portions.

Clause 14: The needleless connector of Clause 13, wherein a distance between the circumferential lip seal and the secondary seal portion is smaller than a distance between the circumferential lip seal and the primary seal portion.

Clause 15: The needleless connector of Clause 13, wherein a distance that the circumferential lip seal extends radially outward from the outer surface of the head portion is smaller than a distance between the circumferential lip seal and the secondary seal portion.

Clause 16: The needleless connector of Clause 12, wherein a diameter of the circumferential lip seal is greater than a diameter of the inner surface at the inlet port.

Clause 17: The needleless connector of Clause 16, wherein the circumferential lip seal comprises a flexible member which engages the inner surface of the housing at the inlet port to deflect to an inverted shape as the valve member reciprocates within the housing between the open state and a closed state.

Clause 18: The needleless connector of Clause 12, wherein the top section includes a top planar surface and the circumferential lip seal is oriented parallel to the top planar surface.

Clause 19: The needleless connector of Clause 12, wherein the top section includes a top planar surface and the circumferential lip seal is oriented at a non-parallel angle with respect to the top planar surface.

Clause 20: The needleless connector of Clause 12, wherein the head portion further comprises a column section defining an axial center of the head portion, and the circumferential lip seal is oriented substantially perpendicularly with respect to the axial center of the head portion.

Clause 21: The needleless connector of Clause 12, wherein the head portion further comprises a column section defining an axial center of the head portion, and the circumferential lip seal is oriented at a non-perpendicular angle with respect to the axial center of the head portion.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A valve member for a connector, the valve member comprising:
    a head portion including a top section and an outer side surface, the outer side surface comprising a notch and a circumferential lip seal, the top section defining a first seal portion extending radially outward from the outer side surface, and the circumferential lip seal extending radially from the outer side surface and comprising a continuous perimeter; and
    a body portion having a proximal end forming a second seal portion and extending longitudinally from the head portion to a distal end of the body portion, wherein the circumferential lip seal is disposed between the first and second seal portions and is flexible such that the circumferential lip seal can deflect toward or away from the first seal portion.

2. The valve member of claim 1, wherein a distance between the circumferential lip seal and the first seal portion is smaller than a distance between the circumferential lip seal and the second seal portion.

3. The valve member of claim 1, wherein a distance that the circumferential lip seal extends radially outward from the outer side surface of the head portion is smaller than a distance between the circumferential lip seal and the first seal portion.

4. The valve member of claim 1, wherein the top section includes a top planar surface and the circumferential lip seal is oriented parallel to the top planar surface.

5. The valve member of claim 1, wherein the top section includes a top planar surface and the circumferential lip seal is oriented at a non-parallel angle with respect to the top planar surface.

6. The valve member of claim 1, wherein the head portion further comprises a column section defining an axial center of the head portion, and the circumferential lip seal is oriented substantially perpendicularly with respect to the axial center of the head portion.

7. The valve member of claim 1, wherein the head portion further comprises a column section defining an axial center of the head portion, and the circumferential lip seal is oriented at a non-perpendicular angle with respect to the axial center of the head portion.

8. The valve member of claim 1, wherein the head portion further comprises a column section defining an axial center of the head portion, and wherein the notch is an arcuate-shaped recess within the column section.

9. The valve member of claim 1, wherein at least one of the head portion or the circumferential lip seal comprises an elastomeric material.

10. The valve member of claim 1, wherein the circumferential lip seal comprises silicone or a silicone compound.

11. The valve member of claim 1, wherein the body portion is shaped as an elongate tubular member having an open end at the distal end of the body portion and a closed end proximal to the second seal portion of the body portion.

12. A needleless connector, comprising:
a housing having a proximal end defining an inlet port of the housing, a distal end defining an outlet port of the housing, and an inner surface defining an internal cavity extending between the inlet and outlet ports; and
a valve member disposed within at least a portion of the internal cavity and movably retained within the housing, the valve member comprising a head portion and a body portion, the head portion including a top section and an outer side surface, the outer side surface comprising a notch and a circumferential lip seal, the top section defining a first seal portion extending radially outward from the outer side surface, and the circumferential lip seal extending radially from the outer side surface and comprising a continuous perimeter, and the body portion having a proximal end forming a second seal portion and extending longitudinally from the head portion to a distal end of the body portion, wherein the circumferential lip seal is disposed between the first and second seal portions and is flexible such that the circumferential lip seal can deflect toward or away from the first seal portion;
wherein, in a closed state of the valve member, the first seal portion and the continuous perimeter of the circumferential lip seal is engaged against the inner surface of the housing, and in an open state of the valve member, a gap is formed between the inner surface of the housing and the first seal portion of the head portion, and the continuous perimeter of the circumferential lip seal is engaged against at least a portion of the inner surface of the housing to obstruct fluid from flowing from the internal cavity towards the first seal portion, wherein the circumferential lip seal deflects toward the inlet port of the housing when the valve member moves from the closed state toward the open state.

13. The needleless connector of claim 12, wherein a distance between the circumferential lip seal and the first seal portion is smaller than a distance between the circumferential lip seal and the second seal portion.

14. The needleless connector of claim 12, wherein a distance that the circumferential lip seal extends radially outward from the outer side surface of the head portion is smaller than a distance between the circumferential lip seal and the first seal portion.

15. The needleless connector of claim 12, wherein a diameter of the circumferential lip seal is greater than a diameter of the inner surface at the inlet port.

16. The needleless connector of claim 15, wherein the circumferential lip seal deflects to an inverted shape as the valve member reciprocates within the housing between the open state and the closed state.

17. The needleless connector of claim 12, wherein the top section includes a top planar surface and the circumferential lip seal is oriented parallel to the top planar surface.

18. The needleless connector of claim 12, wherein the top section includes a top planar surface and the circumferential lip seal is oriented at a non-parallel angle with respect to the top planar surface.

19. The needleless connector of claim 12, wherein the head portion further comprises a column section defining an axial center of the head portion, and the circumferential lip seal is oriented substantially perpendicularly with respect to the axial center of the head portion.

20. A method for providing a needleless connector comprising:
providing a housing having a proximal end defining an inlet port of the housing, a distal end defining an outlet port of the housing, and an inner surface defining an internal cavity extending between the inlet and outlet ports; and
providing a valve member comprising a head portion and a body portion, the head portion including a top section and an outer side surface, the outer side surface comprising a notch and a circumferential lip seal, the top section defining a first seal portion extending radially outward from the outer side surface, and the circumferential lip seal extending radially from the outer side surface and comprising a continuous perimeter, and the body portion having a proximal end forming a second seal portion and extending longitudinally from the head portion to a distal end of the body portion, wherein the circumferential lip seal is disposed between the first and second seal portions;
wherein the valve member is disposed within at least a portion of the internal cavity such that the head portion and the circumferential lip seal are movable relative to the inlet port.

* * * * *